(12) United States Patent
Pacetti et al.

(10) Patent No.: US 6,695,920 B1
(45) Date of Patent: Feb. 24, 2004

(54) MANDREL FOR SUPPORTING A STENT AND A METHOD OF USING THE MANDREL TO COAT A STENT

(75) Inventors: Stephen D. Pacetti, San Jose, CA (US); Mohammed E. Moein, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/894,248

(22) Filed: Jun. 27, 2001

(51) Int. Cl.[7] .............................................. B05C 13/02
(52) U.S. Cl. ..................................................... 118/500
(58) Field of Search ........................ 118/500; 623/1.46, 623/1.47, 148; 427/2.24, 2.25, 2.28, 2.3

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 5,895,407 A | * 4/1999 | Jayaraman | 623/1 |
| 5,897,911 A | 4/1999 | Loeffler | 427/2.25 |
| 6,214,115 B1 | * 4/2001 | Taylor et al. | 118/423 |

* cited by examiner

Primary Examiner—Laura Edwards
(74) Attorney, Agent, or Firm—Squire, Sanders & Dempsey, L.L.P.

(57) ABSTRACT

A mandrel for supporting a stent and a method of applying a coating to the stent supported by the mandrel are disclosed.

14 Claims, 2 Drawing Sheets

MANDREL FOR SUPPORTING A STENT AND A METHOD OF USING THE MANDREL TO COAT A STENT

BACKGROUND OF THE INVENTION

1. Field of the Invention

This invention relates to a mandrel for supporting a stent and a method of applying a coating to the stent supported by the mandrel.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the needed coating from the stent and leaving bare areas. Alternatively, the excess coating may stick to the stent, thereby leaving excess coating as clumps or pools on the struts or webbing between the struts.

Thus, it is desirable to minimize the interface between the stent and the apparatus supporting the stent during the coating process to minimize coating defects. Accordingly, the present invention provides for a device for supporting a stent during the coating application process. The invention also provides for a method of coating the stent supported by the device.

SUMMARY OF THE INVENTION

The present invention provides a mandrel for supporting a stent. The mandrel includes a body for extending at least partially into a hollow stent for supporting the stent during the process of coating the stent. The body has a first section of a first size and a second section of a second size, the second size being greater than the first size. The body can be attached to a motor for providing rotational motion.

In one embodiment, the first section is longer than the second section. In another embodiment, the first section does not make contact with the inner surface of the stent. In still another embodiment, the second size includes a diameter that is less than the inner diameter of the stent.

Also provided is a device for supporting a stent. The device includes a mandrel capable of extending at least partially through a hollow body of a stent and a gear supported by the mandrel for rotating the stent during the process of coating the stent. The gear can include teeth. The gear can also include a textured or roughened surface.

In one embodiment, the positioning of the gear on the mandrel can be adjusted. In another embodiment, the diameter of the gear is greater than the diameter of the mandrel, and the diameter of the gear is less than the inner diameter of the stent. Accordingly, the outer surface of the mandrel does not contact the inner surface of the stent.

The present invention also provides a method of coating a stent. The method includes positioning a stent on a mandrel having a gear member. The method additionally includes rotating the mandrel to cause the gear member to provide rotational motion to the stent and applying a coating material to the stent. In one embodiment, the act of applying includes spraying a composition including a polymer added to a fluid and optionally an active agent added thereto onto the stent.

DETAILED DESCRIPTION

Embodiments of the Mounting Assembly

Various types of coating defects can arise due to permanent contact points between a stent and its supporting apparatus. The present invention minimizes or eliminates such coating defects by having no permanent contact points between a stent and its supporting apparatus during the coating process.

Figure 1:
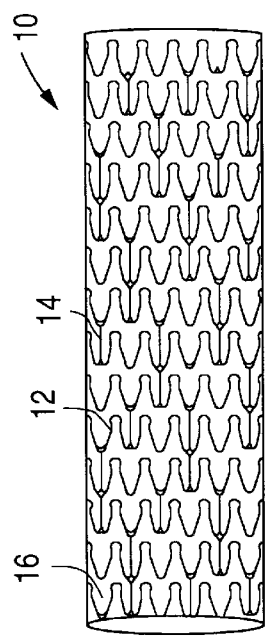
FIG. 1 illustrates a conventional stent.
Figure 2A:
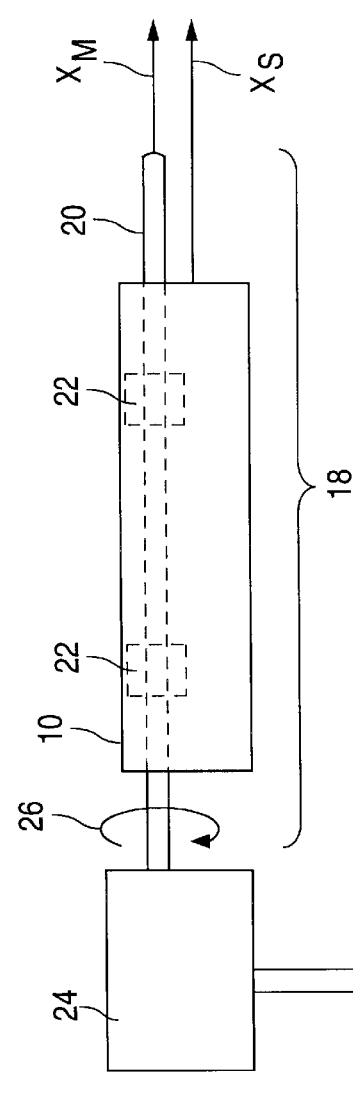
FIG. 2A illustrates a mounting assembly for supporting a stent.

Referring to FIG. 2A, a mounting assembly 18 for supporting stent 10 is illustrated to include a rod or mandrel 20 and gear members 22. Mandrel 20 can connect to a motor 24, which provides rotational motion to mandrel 20, as depicted by arrow 26, during the coating process. Another motor 28 can also be provided for moving mandrel 20 and thus stent 10 in a linear direction, back and forth, along a rail 30.

Mandrel 20 is illustrated as having two regions with a larger diameter. The two regions can be gear members 22 for applying a torque to stent 10. In commercially useful embodiments, any number of gear members 22 can be used to adequately support stent 10, and the embodiments of the present invention should not be limited to a mandrel 20 having merely two gear members 22 as illustrated in the Figures. Gear members 22 should be sized larger than the outer diameter of mandrel 20 so as to prevent mandrel 20 from being in contact with the inner surface of stent 10. Additionally, gear members 22 should be sized smaller than the inner diameter of stent 10 so as to provide for minimum contact between gear members 22 and the inner surface of stent 10. Providing gear members 22 of small diameter, as compared to the inner diameter of stent 10, offsets an axis $x_M$, about which gear members 22 rotate, away from an axis $x_S$, about which stent 10 rotates—axis $x_S$ being positioned longitudinally through the center of stent 10. Exemplary specifications that can be employed with stent 10 having a length of about 18 mm and an inner diameter of about 1.8 mm include:

| Component | Length (mm) | Diameter (mm) |
|---|---|---|
| Mandrel | 40 | 0.38 |
| Gear member | 1.5 | 0.9 |

Figure 2B:
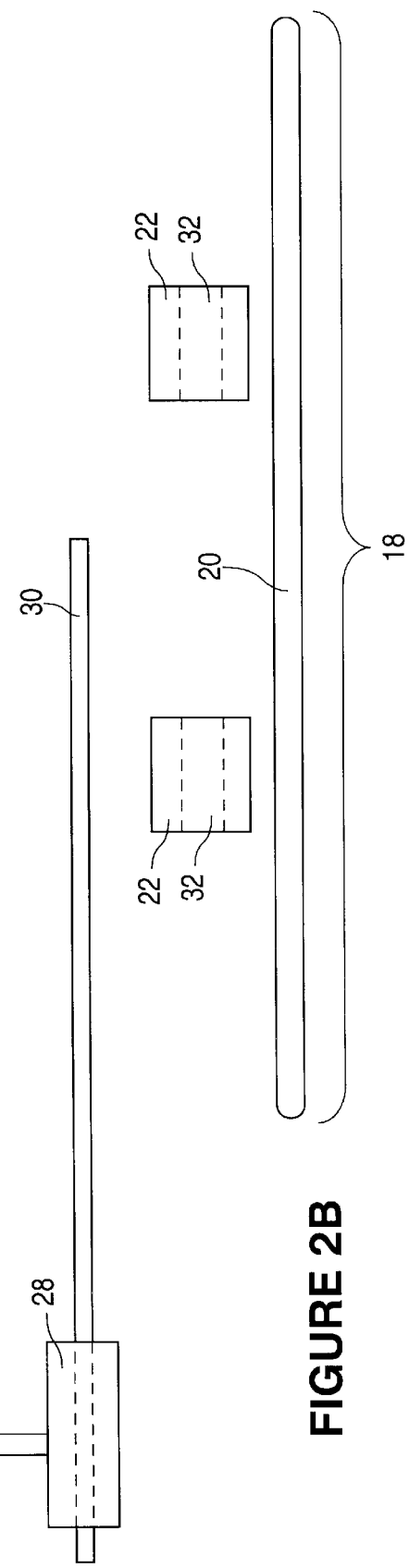
FIG. 2B illustrates an expanded view of the mounting assembly in accordance with one embodiment of the present invention.

In accordance with one embodiment, gear members 22 can be permanently affixed to mandrel 20. Alternatively, gear members 22 can be adjustably coupled to mandrel 20. As illustrated in FIG. 2B, in such an embodiment, gear members 22 can include bores 32 for receiving mandrel 20. Bores 32 can extend completely through gear members 22. By way of example, mandrel 20 and bores 32 can be threaded such that the clockwise or counterclockwise rotation of gear members 22 would allow the user to adjust the location of gear members 22 along mandrel 20 to most suitably support stent 10.

Figures 3A, 3B:
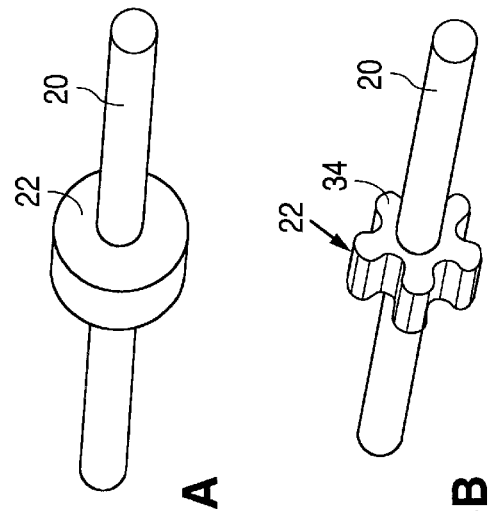
FIGS. 3A and 3B are perspective views of the gear members of the mounting assembly in accordance with various embodiments of the present invention.

The body of gear members 22 can be of any suitable shape. For example, gear members 22 can be without teeth, as illustrated in FIG. 3A, or can include teeth 34, as illustrated in FIG. 3B. The number, size, and spacing of teeth 34 can be selected to coordinate with the type of stent 10 employed. In addition, the outer surface of gear members 22 can be textured or roughened for creating suitable friction against the inner surface of stent 10. However, the texture of the outer surface of gear members 22 should not be so rough or jagged as to cause any damage to the inner surface of stent 10.

Figure 4:
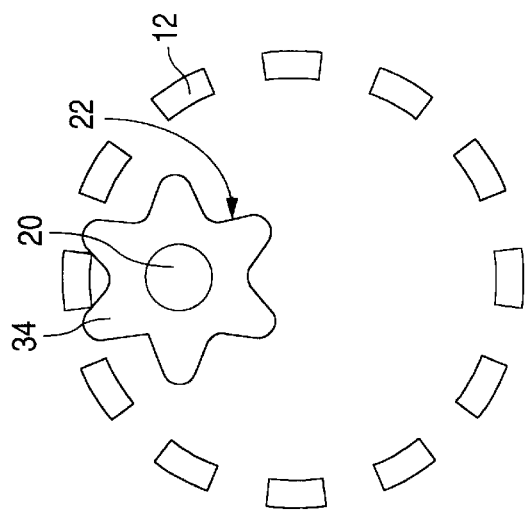
FIG. 4 is an end view of the interface between the mounting assembly and the stent in accordance with one embodiment of the present invention.

FIG. 4 illustrates the contact interface between gear member 22 and stent 10. Gear member 22 is in minimum contact with stent 10. Moreover, the revolution of stent 10 about gear member 22 allows the contact points between stent 10 and mounting assembly 18 to be transient rather than permanent, thereby preventing the coating material from flowing, wicking, collecting, and solidifying at or between gear member 22 and stent 10.

Figure 5:
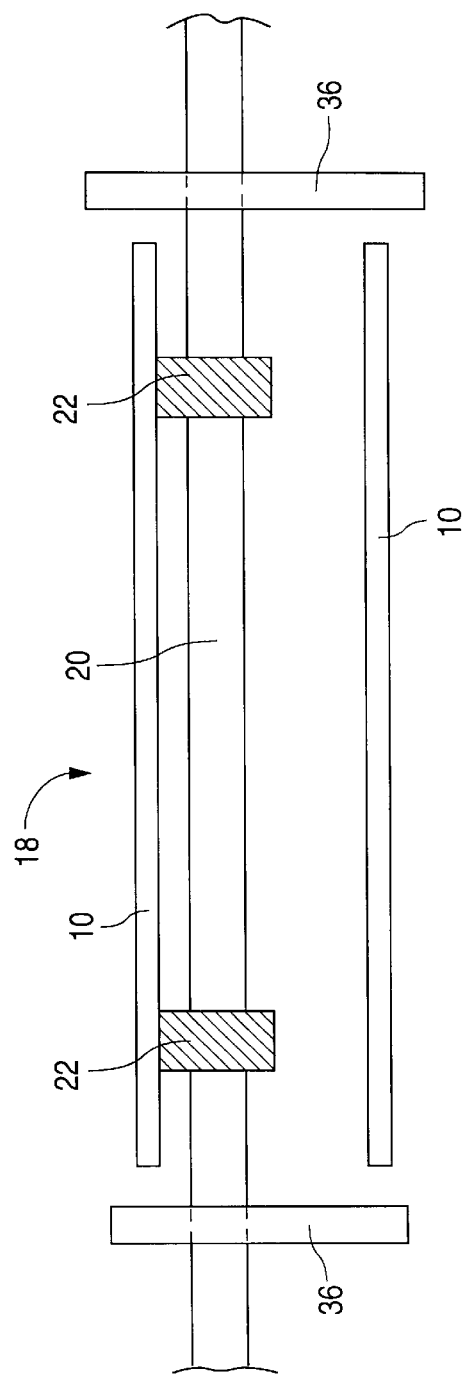
FIG. 5 is a cross-sectional view of the interface between the mounting assembly and the stent in accordance with one embodiment of the present invention.

FIG. 5 is a cross-sectional view of the interface between stent 10 and mounting assembly 18. In one embodiment, optional barrier members 36 can be employed so as to prevent stent 10 from sliding off of mounting assembly 18. Barrier members 36 can be spaced at a distance from stent 10 so as to prevent collection of coating material between barrier members 36 and the ends of stent 10. At least one barrier member 36 should be disengagable from mandrel 20 so as to allow mounting and dismounting of stent 10.

Coating a Stent Using the Mounting Assembly

The following method of application is being provided by way of illustration and is not intended to limit the embodiments of mounting assembly 18 of the present invention. A spray apparatus, such as EFD 780S spray device with VALVEMATE 7040 control system (manufactured by EFD Inc., East Providence, R.I.), can be used to apply a composition to a stent. EFD 780S spray device is an air-assisted external mixing atomizer. The composition is atomized into small droplets by air and uniformly applied to the stent surfaces. The atomization pressure can be maintained at a range of about 5 psi to about 20 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition.

During the application, of the composition, mandrel 20 can be rotated about its own central longitudinal axis. Rotation of mandrel 20 can be from about 10 rpm to about 300 rpm, more narrowly from about 40 rpm to about 240 rpm. By way of example, mandrel 20 can rotate at about 100 rpm. Mandrel 20 can also be moved in a linear direction along the same axis. Mandrel 20 can be moved at about 1 mm/second to about 6 mm/second, for example about 3 mm/second, or for a minimum of at least two passes (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/cm$^2$ (of stent surface) to about 40 micrograms/cm$^2$, for example less than about 2 micrograms/cm$^2$ per 5-second spray.

Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2–4 hours) or by the application of warm air. The application of warm air between each repetition prevents coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer in a single application can, however, cause coating defects.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

In accordance with one embodiment, the composition can include a solvent and a polymer dissolved in the solvent. The composition can also include active agents, radiopaque elements, or radioactive isotopes. Representative examples of polymers that can be used to coat a stent include ethylene vinyl alcohol copolymer (commonly known by the generic name EVOH or by the trade name EVAL), poly (hydroxyvalerate); poly(L-lactic acid); polycaprolactone; poly(lactide-co-glycolide); poly(hydroxybutyrate); poly (hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly (iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. Exposure of the active ingredient to the composition should not adversely alter the active ingredient's composition or characteristic. Accordingly, the particular active ingredient is selected for compatibility with the solvent or blended polymer-solvent.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A device for supporting a stent, comprising:
   a mandrel capable of extending through a hollow body of a stent and attachable to a rotating apparatus; and
   a gear supported by the mandrel, the gear having a diameter greater than a diameter of the mandrel and positioned on the mandrel to support the stent on an inner surface of the stent and to provide sufficient torque to the stent for rotating the stent during a coating process, wherein the gear includes a textured or roughened surface.

2. The device of claim 1, wherein the positioning of the gear on the mandrel can be adjusted.

3. The device of claim 1, wherein the diameter of the gear is less than an inner diameter of the stent.

4. The device of claim 1, wherein an outer surface of the mandrel does not contact the inner surface of the stent.

5. A device for supporting a stent, comprising:
   a mandrel capable of extending through a hollow body of a stent and attachable to a rotating apparatus; and
   a gear supported by the mandrel, the gear having a diameter greater than a diameter of the mandrel and positioned on the mandrel to support the stent on an inner surface of the stent and to provide sufficient torque to the stent for rotating the stent during a coating process, wherein the gear includes teeth.

6. A device for supporting a stent, comprising:
   a mandrel capable of extending through a hollow body of a stent and attachable to a rotating apparatus; and
   a gear supported by the mandrel, the gear having a diameter greater than a diameter of the mandrel and positioned on the mandrel to support the stent on an inner surface of the stent and to provide sufficient torque to the stent for rotating the stent during a coating process, wherein the stent comprises struts and gaps disposed in between the struts, and wherein the gear includes teeth sized to fit into the gaps of the stent.

7. A longitudinal mounting device for rotating a stent during a coating process, comprising:
   a mandrel having a first end and a second end and attachable to a rotating apparatus; and
   a gear located between the first and second ends, the gear configured to allow a stent to rest thereon so as to form a contact area between an outer surface of the gear and an inner surface of the stent, wherein a shape or diameter of the gear is configured so that the contact area changes location as the stent is rotated.

8. The mounting device of claim 7, further comprising a second gear between the first and second ends of the mandrel, wherein the second gear is configured to allow the stent to rest thereon.

9. The mounting device of claim 7, wherein the gear is substantially circular along an outer circumference of the gear.

10. The mounting device of claim 7, wherein the gear has teeth.

11. The mounting device of claim 7, wherein the gear is removably attached to the mandrel.

12. The mounting device of claim 7, wherein the gear is star-shaped.

13. A mandrel for supporting a stent during a coating process that includes rotating the stent, the mandrel comprising a body extending through a hollow stent, wherein the body includes a textured or roughed surface area for the stent to rest thereon for creating friction against an inner surface of the stent thereby configured to apply torque to the stent as the mandrel is rotated.

14. A device for supporting a stent, comprising:
   a mandrel extending through a hollow body of a stent; and
   a gear supported by the mandrel and positioned to support an inner surface of the stent during a coating process, wherein the gear has a threaded bore to allow the gear to be adjustable along a length of the mandrel.

* * * * *